US 8,697,036 B2

(12) United States Patent
Hoke, II et al.

(10) Patent No.: US 8,697,036 B2
(45) Date of Patent: *Apr. 15, 2014

(54) PROCESS FOR SURFACTANT TASTE AND/OR ODOR IMPROVEMENT

(75) Inventors: Steven Hamilton Hoke, II, West Chester, OH (US); John Christian Haught, West Chester, OH (US); Brian David Clair, Ft. Wright, KY (US); Marc Alan Hester, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/564,823

(22) Filed: Aug. 2, 2012

(65) Prior Publication Data
US 2013/0034508 A1 Feb. 7, 2013

Related U.S. Application Data

(60) Provisional application No. 61/514,213, filed on Aug. 2, 2011.

(51) Int. Cl.
| | | |
|---|---|---|
| *A61K 8/30* | (2006.01) | |
| *A61Q 11/00* | (2006.01) | |
| *A61K 8/46* | (2006.01) | |
| *A61K 8/55* | (2006.01) | |
| *A61K 8/41* | (2006.01) | |

(52) U.S. Cl.
USPC .............................................. 424/49; 424/57

(58) Field of Classification Search
None
See application file for complete search history.

(56) References Cited

U.S. PATENT DOCUMENTS

| | | | |
|---|---|---|---|
| 4,352,829 A | | 10/1982 | Noyes et al. |
| 4,389,300 A | * | 6/1983 | Mitchell ........................ 208/390 |
| 4,804,533 A | * | 2/1989 | Imamura et al. ................. 424/69 |
| 5,292,502 A | * | 3/1994 | Burke et al. ..................... 424/54 |
| 5,322,643 A | | 6/1994 | Schwartz et al. |
| 5,407,921 A | * | 4/1995 | Katsuragi et al. ................ 514/75 |
| 5,807,516 A | | 9/1998 | Cottrell et al. |
| 2002/0010104 A1 | | 1/2002 | Ewbank et al. |
| 2007/0123445 A1 | | 5/2007 | Tuzi et al. |
| 2008/0008667 A1 | * | 1/2008 | Hoke et al. ....................... 424/58 |
| 2009/0214711 A1 | * | 8/2009 | Bayani ............................. 426/66 |
| 2010/0069477 A1 | | 3/2010 | Itoh et al. |

FOREIGN PATENT DOCUMENTS

| | | |
|---|---|---|
| FR | 2 733 982 A1 | 11/1996 |
| WO | WO94/09108 A1 | 4/1994 |
| WO | WO 98/26036 A1 | 6/1998 |
| WO | WO 00/06690 A1 | 2/2000 |
| WO | WO 2008/005550 A2 | 1/2008 |

OTHER PUBLICATIONS

Hansen, Charles. Hansen Solubility Parameters: A User's Handbook. (2007). CRC Press. p. 280.*
Elmhurst College. Temperature and Pressure Effects on Solubility. May 18, 2011. p. 1.*
International Search Report for PCT/US2012/049332, dated Nov. 22, 2012.
International Search Report for PCT/US2012/049314, dated Dec. 10, 2012.

* cited by examiner

*Primary Examiner* — Lezah Roberts
*Assistant Examiner* — Tracy Liu
(74) *Attorney, Agent, or Firm* — Armina E. Stricklin

(57) ABSTRACT

Processes for improving the taste of water-soluble surfactants using liquid-liquid solvent extraction, said process comprising the steps of: providing a water-soluble surfactant composition in need of treatment wherein said water-soluble surfactant composition comprises a water-soluble surfactant and one or more undesirable non-polar materials; contacting said water-soluble surfactant composition with an extraction solvent and water to form an extraction mixture comprising an aqueous phase and a solvent phase; and separating the aqueous phase from the solvent phase; wherein the extraction solvent is selected from solvents having individual Hansen solubility parameters of a dispersion force component ($\delta_D$) ranging from about 15 to about 17 $(MPa)^{0.5}$, a polar component ($\delta_P$) ranging from 0 to about 9 $(MPa)^{0.5}$ and a hydrogen bonding component ($\delta_H$) ranging from 0 to about 11 $(MPa)^{0.5}$. Treated water-soluble surfactant compositions produced by such processes and oral care compositions containing such treated water-soluble surfactant compositions.

22 Claims, 1 Drawing Sheet

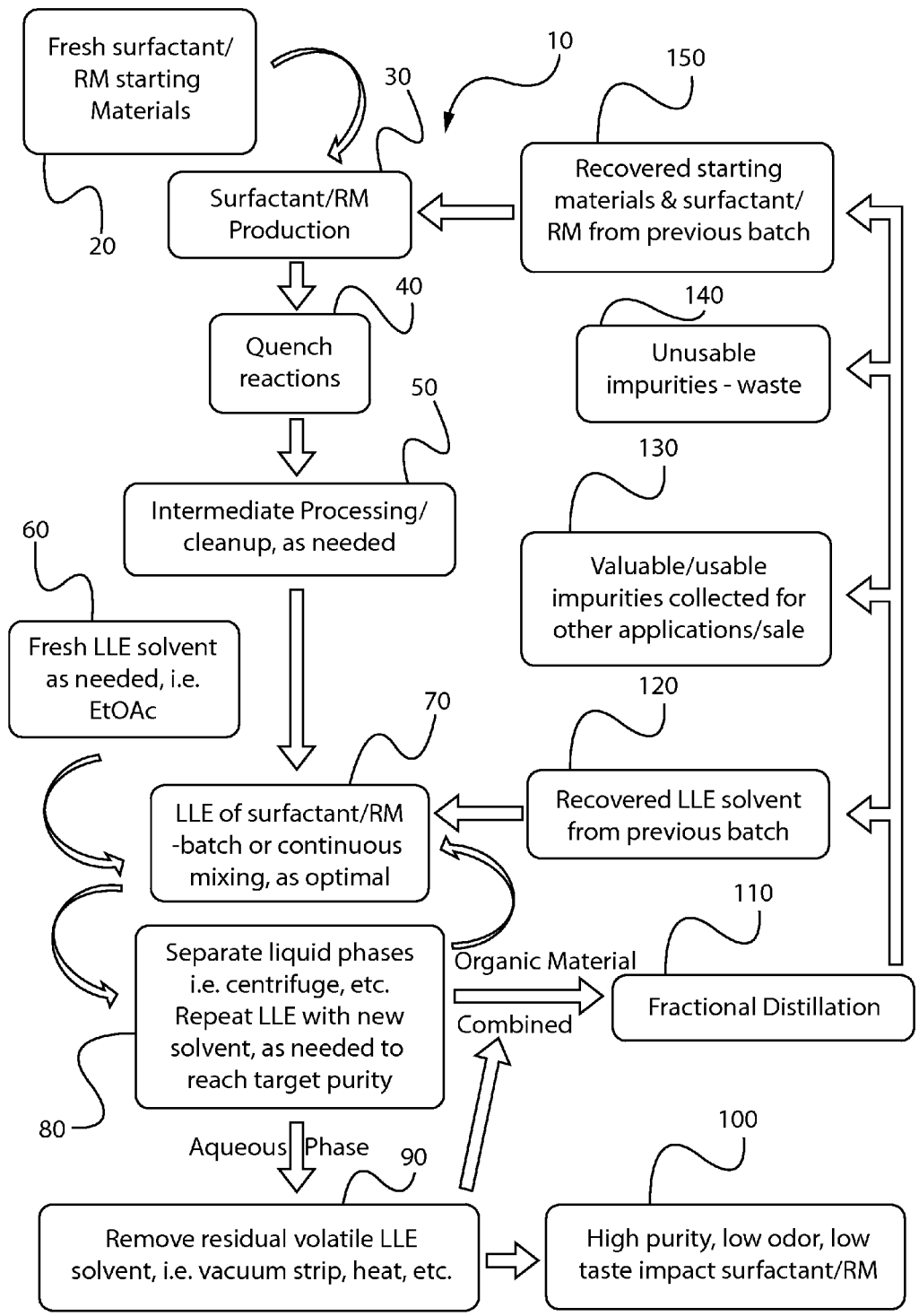

PROCESS FOR SURFACTANT TASTE AND/OR ODOR IMPROVEMENT

CROSS REFERENCE TO RELATED APPLICATION

This reference claims priority to U.S. Provisional Application No. 61/514,213, filed on Aug. 2, 2011, which is incorporated herein by reference.

FIELD OF THE INVENTION

The present invention relates to water-soluble surfactant compositions containing undesirable non-polar materials and liquid-liquid extraction processes for improving the taste and/or odor of such compositions.

BACKGROUND OF THE INVENTION

Traditionally, much effort has been expended to improve the taste, color, odor or clarity of oral care compositions such as dentifrice (toothpaste), mouth rinse, and the like. Because of the nature of such compositions, the taste of a product may often be of more importance to consumers than the actual or perceived efficacy. Since many efficacious oral care components have undesirable taste, color, odor or clarity, efforts to improve these characteristics are common in the art. For taste, one way to remedy an undesirable product taste is to add additional components, such as flavors, that will improve the overall taste experience for the consumer. However, such remedies can be expensive and it may be difficult to entirely mask an undesirable taste. Improvement of color or clarity through dyes or other additives has similar issues.

Water-soluble surfactants such as alkyl phosphate surfactants are commercially available for use in a variety of consumer products, including oral care compositions. These anionic surface active organophosphate agents have a strong affinity for enamel surface and have sufficient surface binding propensity to desorb pellicle proteins and remain affixed to enamel surfaces. Such properties make these materials desirable for incorporation in oral care compositions such as toothpaste. However, these materials have not been widely commercialized in oral care compositions, despite their desirable properties. One reason for this lack of commercialization may be the negative taste and/or odor profile commonly associated with commercially available alkyl phosphate materials. Although taste may not be a consideration in other consumer product industries, such as laundry, shampoo or personal cleansing, it is an important consideration in oral care. Similarly, while any undesirable odor associated with materials used in laundry, shampoo or personal cleansing products can typically be remedied by the addition of perfume, perfume levels must be kept to a minimum in oral care compositions for consumer acceptance and could produce further unpleasant tastes when utilized.

Purification of surfactant materials through steam-stripping, vacuum-stripping, and/or carbon filtration processes is also generally known to beneficially remove impurities to increase efficacy, minimize undesirable side reactions, and the like. However, these purification processes have been found to be insufficient to remedy the unpleasant tastes and/or odors associated with commercially available water-soluble surfactant materials.

Liquid/liquid extractions (LLE) are generally known in the art as useful for separating components of a mixture, wherein the constituents have differing polarities which can be separated when mixed within two immiscible solvents that form a liquid bilayer after mixing. For example, LLEs are useful for purifying or cleaning samples which contain impurities of significantly differing polarity than the majority or desirable component(s) of the sample. This can be achieved by mixing a sample with a solvent that is immiscible with the primary liquid in which the sample is dissolved.

LLE has been utilized in chemical processing to reduce or eliminate undesirable by-products or contaminants. For instance, PCT Patent Application WO 2008005550 to Hoke, et al (Procter & Gamble) discloses a water washing procedure to remove polar sulfur impurities from peppermint oils to avoid malodor formation when formulated in dentifrice containing stannous ions. In U.S. Pat. No. 4,352,829 to Noyes, et al (Procter & Gamble) an ethyl acetate extraction of caffeine from coffee was shown to be an effective decaffeination process.

However, there is still an interest in finding ways to improve the overall taste and/or odor of water-soluble surfactants such as those used in an oral care composition that are efficacious, cost-effective, and desirable to consumers.

SUMMARY OF THE INVENTION

It has now surprisingly been found that liquid-liquid extraction processes utilizing solvents such as ethyl acetate may be useful to significantly reduce the occurrence of non-polar materials found in water-soluble surfactant raw materials and thereby improve the surfactant's odor and/or taste profile.

Without being limited by theory, it is now believed that water-soluble surfactants previously generally thought to have bad taste and/or odor profiles stemming from the pure material itself are in fact surprisingly acceptable in terms of taste and odor. It has been surprisingly found that non-polar materials commonly present in commercially available water-soluble surfactant compositions such as residual alcohols, alcohol ethoxylates, aldehydes, ethers, ketones, alkylamines, and esters, may be linked to the majority of the negative taste and odor profiles previously associated with the surfactants themselves. Since some of these materials are often used in flavors and perfumes, it was further surprising that a new process for more efficiently extracting these materials from the underlying surfactant would produce such results. For example, dodecanol and dodecanal are commonly taught to be safe and useful for inclusion in flavors and perfumes, yet it has been surprisingly found that if included in water-soluble surfactant compositions at significantly higher levels, these materials present an unpleasant taste such as bitter, soapy and the like.

Further without being limited by theory, liquid-liquid extraction using the appropriate solvent is more effective than previously known techniques to purify such surfactants, allowing for the incorporation of such surfactants into oral care products with minimal negative taste and/or odor attributes.

The present invention is therefore directed to a process or method of improving the taste and/or odor of water-soluble surfactants using liquid-liquid solvent extraction.

In one embodiment, the present invention relates to a process or method for improving the taste of water-soluble surfactants using liquid-liquid solvent extraction, said process comprising the steps of: providing a water-soluble surfactant composition in need of treatment wherein said water-soluble surfactant composition comprises a water-soluble surfactant and one or more undesirable non-polar materials; contacting said water-soluble surfactant composition with an extraction solvent and water to form an extraction mixture comprising an aqueous phase and a solvent phase; and separating the aqueous phase from the solvent phase; wherein the extraction solvent is selected from solvents having individual Hansen solubility parameters of a dispersion force component ($\delta_D$) ranging from about 15 to about 17 (MPa)$^{0.5}$, a polar component ($\delta_P$) ranging from 0 to about 9 (MPa)$^{0.5}$ and a hydrogen bonding component ($\delta_H$) ranging from 0 to about 11 (MPa)$^{0.5}$.

In another embodiment, the present invention relates a process or method for improving the taste of water-soluble surfactants using liquid-liquid solvent extraction, said process comprising the steps of: providing a water-soluble surfactant composition comprising a surfactant selected from alkyl phosphate surfactants, alkyl phosphate ethoxylated surfactants, and mixtures thereof and one or more undesirable non-polar materials; contacting said water-soluble surfactant composition with ethyl acetate and water to form an extraction mixture comprising an aqueous phase and a solvent phase; and separating the aqueous phase from the solvent phase.

In another embodiment, the present invention relates to such processes or methods wherein the water-soluble surfactant is at least about 20% soluble in water.

In another embodiment, the present invention relates to the above processes or methods wherein the water-soluble surfactant is selected from anionic surfactants, zwitterionic surfactants, amphoteric surfactants, and mixtures thereof and is at least about 30% soluble in water.

In another embodiment, the present invention relates to the above processes or methods wherein the water-soluble surfactant is selected from alkyl phosphate surfactants, alkyl phosphate ethoxylated surfactants, lauryl sulfate surfactants, betaine surfactants, betaine ethoxylated surfactants, amine oxide surfactants, and mixtures thereof.

In another embodiment, the present invention relates to the above processes or methods wherein the surfactant is selected from cocoamidopropyl betaines, lauryl betaines, capryl/capramidobetaines, sodium lauryl sulfates, mono alkyl phosphates, amine oxides, and mixtures thereof.

In another embodiment, the present invention relates to the above processes or methods wherein the water-soluble surfactant is selected from cocoamidopropyl betaine surfactants, mono alkyl ethoxylated phosphate surfactants, mono alkyl phosphate surfactants, and mixtures thereof.

In one embodiment, the water-soluble surfactant is an alkyl ethoxylated phosphate surfactant.

In another embodiment, the present invention relates to the above processes or methods wherein the extraction solvent has individual Hansen solubility parameters of a dispersion force component ($\delta_D$) ranging from about 13 to about 19 (MPa)$^{0.5}$, a polar component ($\delta_P$) ranging from about 2 to about 9 (MPa)$^{0.5}$ and a hydrogen bonding component ($\delta_H$) ranging from about 2 to about 11 (MPa)$^{0.5}$.

In another embodiment, the present invention relates to the above processes or methods wherein the extraction solvent is selected from ethyl acetate, water-saturated ethyl acetate, ethyl propionate, ethyl butyrate, ethyl pentanoate, ethyl caproate, ethyl caprylate, ethyl pelargonate methyl acetate, methyl propionate, methyl butyrate, short chain esters and mixtures thereof.

In another embodiment, the present invention relates to the above processes or methods wherein the extraction solvent is selected from food grade ethyl esters.

In another embodiment, the present invention relates to the above processes or methods wherein the extraction solvent is ethyl acetate.

In another embodiment, the present invention relates to the above processes or methods wherein the extraction mixture comprises from about 10% to about 90%, by weight of the mixture, of water; from about 5% to about 60%, by weight of the mixture, of water-soluble surfactant; less than 5%, by weight of the mixture, of undesirable non-polar impurities; and from about 10% to about 90%, by weight of the mixture, of solvent.

In another embodiment, the present invention relates to the above processes or methods wherein the ratio of extraction solvent to water-soluble surfactant in the extraction mixture is from about 1:10 to about 10:1.

In another embodiment, the present invention relates to the above processes or methods wherein the ratio of extraction solvent to water-soluble surfactant in the extraction mixture is from about 1:2 to about 2:1.

In another embodiment, the present invention relates to the above processes or methods wherein the step of separating the aqueous phase from the solvent phase further comprises centrifuging the extraction mixture.

In another embodiment, the present invention relates to the above processes or methods wherein the process further comprises mixing extraction mixture is mixed for a period of from about 10 seconds to about one minute with vigorous mixing and at ambient temperature before allowing the mixture to settle into two phases and separating the aqueous phase from the solvent phase.

In another embodiment, the present invention relates to the above processes or methods wherein the process further comprises the step of heating a solid impure surfactant material to its melting point before the step of contacting with an extraction solvent and water.

In another embodiment, the present invention relates to the above processes or methods wherein the process further comprises the step of removing any residual solvent from the aqueous phase.

In another embodiment, the present invention relates to the above processes or methods wherein the step of removing any residual solvent from the aqueous phase includes the use of an industrial method selected from vacuum stripping (with or without heat), wiped-film evaporation fractional distillation, carbon filtration, or combinations thereof.

In another embodiment, the present invention relates to the above processes or methods wherein the extraction mixture further comprises a phase separation enhancer selected from salt, pH modifiers, and mixtures thereof.

In another embodiment, the present invention relates to a treated water-soluble surfactant composition resulting from the above processes or methods comprising from about 10% to about 70% of water-soluble surfactant, from about 30% to about 90% water, and less than about 1% of undesirable non-polar materials, produced by the processes set forth above.

In another embodiment, the present invention relates to such surfactants wherein the surfactant comprises less than about 0.5% of undesirable non-polar materials.

In another embodiment, the present invention relates to such surfactants wherein the surfactant comprises less than about 1% of total alcohols.

In another embodiment, the present invention relates to a treated mono alkyl phosphate surfactant produced by the processes or methods set forth above.

In another embodiment, the present invention relates to a treated cocoamidopropyl betaine surfactant produced by the processes or methods set forth above.

In another embodiment, the present invention relates to an oral care composition having improved consumer acceptance, wherein the oral care composition comprises a water-soluble surfactant composition treated by the processes set forth above In another embodiment, the present invention relates to use of liquid-liquid solvent extraction for improving the taste of water-soluble surfactants wherein ethyl acetate is used as an extraction solvent.

BRIEF DESCRIPTION OF THE DRAWINGS

FIG. 1 is a flow diagram of a process for purifying surfactants using liquid-liquid solvent extraction in accordance to one embodiment of the present invention.

DETAILED DESCRIPTION OF THE INVENTION

The present invention relates to a process for improving the taste of water-soluble surfactants using liquid-liquid solvent extraction. The process includes the steps of:
  a) providing a water-soluble surfactant composition in need of treatment wherein said water-soluble surfactant composition comprises a water-soluble surfactant and one or more undesirable non-polar materials;
  b) contacting said water-soluble surfactant composition with an extraction solvent and water to form an extraction mixture comprising an aqueous phase and a solvent phase; and
  c) separating the aqueous phase from the solvent phase;
wherein the extraction solvent is selected from solvents having individual Hansen solubility parameters of a dispersion force component ($\delta_D$) ranging from about 15 to about 17 (MPa)$^{0.5}$, a polar component ($\delta_P$) ranging from 0 to about 9 (MPa)$^{0.5}$ and a hydrogen bonding component ($\delta_H$) ranging from 0 to about 11 (MPa)$^{0.5}$. The present invention further relates to improved water-soluble surfactant compositions produced by the processes herein and oral care compositions containing such improved surfactants.

These elements will be discussed in more detail below.
Process for Improving the Taste of Water-Soluble Surfactants As used herein, liquid-liquid extraction, also known as solvent extraction and partitioning, refers to a standard method to separate compounds based upon their relative solubilities in two different immiscible liquids, here, water and a solvent. It is an extraction of a substance from one liquid phase into another liquid phase. The "liquid-liquid" phrase refers to the two different immiscible liquids that are mixed as part of the extraction procedure. As used herein, immiscible refers to the ability of the two liquids to form at least two layers when mixed together. The layers may be formed after mixing the two liquids and allowing them to sit at rest for a variable period of time, or in some instances, the mixture of the two liquids may be centrifuged and/or cooled below room temperature in order to assist the separation.

Typically in liquid-liquid extraction, one of the phases will be aqueous, and the other a non-polar lipophilic organic solvent such as ether, MTBE, dichloromethane, chloroform, or ethyl acetate. Most organic solvents float on top of an aqueous phase, though important exceptions are most halogenated solvents.

Equipment typically used in a laboratory setting for liquid-liquid extraction includes a separatory funnel. In a small scale plant or lab, batch-wise liquid-liquid extraction methods may be used, such as by mixing the two liquids and then introducing them into a large scale separatory funnel. In larger scale plant production, a multistage continuous counter current extractor may be used to quickly and easily run multiple extractions in sequence. In one embodiment, the process includes the use of a machine selected from centrifugal contactors, thin layer extractors, spray columns, pulsed columns, and mixer-settlers, and combinations thereof, in the extraction process.

In many instances, a separatory funnel has the shape of a cone surmounted by a hemisphere. It has a stopper at the top and stopcock (tap), at the bottom. Separating funnels used in laboratories are typically made from borosilicate glass and their stopcocks are made from glass or PTFE. Typical sizes are between 50 mL and 3 L. In industrial chemistry they can be much bigger and for much larger volumes, centrifuges are used.

To use a separatory funnel, the extraction mixture is introduced into the separatory funnel through the top with the stopcock at the bottom closed. The funnel is then closed and shaken gently by inverting the funnel multiple times. The funnel is then inverted and the tap carefully opened to release excess vapor pressure. The separating funnel is set aside to allow for the complete separation of the phases. The top and the bottom tap are then opened and the two phases are individually released by gravitation and separately captured.

Referring now to FIG. 1, an industrial flow chart detailing the process 10 of making a water-soluble surfactant and then improving the taste of water-soluble surfactants using liquid-liquid extraction, contains a series of steps, step 20 providing fresh surfactant raw material starting materials, step 30 production of the water-soluble surfactant through traditional means, step 40 quenching the reaction, step 50 optional intermediate processing and/or cleanup and providing the water-soluble surfactant composition in need of treatment, step 60 contacting the water-soluble surfactant composition with an extraction solvent, and water step 70 to form an extraction mixture containing an aqueous phase and a solvent phase, step 80 separating the liquid phases with optional centrifuge and optional repeating of steps 60 and 70, step 90 separating residual volatile solvent from the aqueous phase by means such as vacuum stripping, heating, wiped-film evaporation or combinations thereof, step 100, collecting the improved water-soluble surfactant, step 110 conducting fractional distillation on the organic phase to, step 120 recover the extraction solvent for future use, step 130 to collect non-polar materials (impurities) and separate into valuable and 140 unusable non-polar materials (impurities) including the step of 150 recovering the starting surfactant raw materials for reuse.

At step 20 and 30, the water-soluble surfactant raw material, such as those commercially available, is produced. At step 60, the process for improving the taste of such water-soluble surfactant raw material begins by providing the water-soluble surfactant composition in need of treatment wherein the water-soluble surfactant composition contains a water-soluble surfactant and one or more undesirable non-polar materials. By combining the water-soluble surfactant composition with water and solvent forming an extraction mixture and then separating the aqueous phase from the solvent phase in step 80, the treated water-soluble surfactant may be collected, in step 100.

In one embodiment, the liquid-liquid extraction process will use an extraction step in which undesirable non-polar materials are transferred from the aqueous phase to the solvent phase and then optionally followed by a scrubbing stage in which the undesirable non-polar materials are removed from the solvent phase, then optionally followed by a stripping stage in which any water-soluble surfactants or other materials are removed from the solvent phase. The solvent phase may then be treated to make it ready for use again.

In one embodiment, the process includes a step of collecting the water-soluble surfactant from the aqueous phase. In another embodiment, after the step of collecting the water-soluble surfactant from the aqueous phase, the water-soluble surfactant is subjected to one or more of the following:

a) at least one repeat of the process steps, optionally repeating the steps of the process at least 3 times, optionally repeating the steps of the process at least 4 times, in succession;

b) a further filtration step, optionally using carbon filtration; and/or c) incorporation of the water-soluble surfactant into an oral care composition.

Procedure for Optimizing pH in Preparation for Liquid/Liquid Extraction

In one embodiment, the process further comprises a step of optimizing the pH of the extraction mixture. In such a step, the solubility of the water-soluble surfactant composition may be optimized and the polarity difference between the desirable water-soluble surfactant and undesirable non-polar materials that are imparting negative aroma, taste and/or color may be maximized. The pH is an important variable that can be adjusted to maximize the polarity difference between the desirable water-soluble surfactant and the undesirable non-polar materials. This is especially important with classes of compounds that can change from primarily charged to neutral state and vice versa by pH manipulation.

For example, in the case of mono alkyl phosphate surfactants, a higher pH may be preferable to ensure that the phosphate groups are largely in the ionized state, thereby maximizing polarity and water solubility. At the same time, most of the undesirable non-polar materials found in commercially-available MAP compositions would not be significantly ionized at typical pHs, and possess a net hydrophobic character, so in one embodiment, the pH during extraction is optimized to be in the range of 8-11. In one embodiment, the process further comprises an extraction pH of from about 8 to about 11, alternatively from 8 to 10.

Further, a consideration is to avoid pHs that can initiate chemical reactivity, for a given extraction mixture comprising an aqueous phase comprising a water-soluble surfactant raw material dissolved in water, an undesirable non-polar material, and the extraction solvent. For example, when using ethyl acetate as an extraction solvent with mono alkyl phosphate, it is recommended to maintain extraction conditions in a pH range that will avoid converting EtOAc to acetic acid and ethanol. In one embodiment, after extraction, the ethyl acetate should be removed to a level that will be odorless and also avoid the potential for later conversion to significant levels of ethanol and acetic acid, the latter of which may introduce vinegar odors into the raw material. In one embodiment, after extraction, the ethyl acetate is removed to a level of less than 50 ppm, alternatively less than 5 ppm.

General pH optimization can be performed as above. For refined pH optimization, adjust pH in small increments and perform a single stage LLE. After single extractions over the target pH range, analytically measure the amount of water-soluble surfactant and the amount of undesirable non-polar materials in the extraction solvent, with prior knowledge of the starting concentrations of surfactant and non-polar impurities in the water-soluble surfactant composition. Identify the pH range where the impurity removal into the solvent phase is optimal and the surfactant retention in the aqueous phase is also optimal.

Providing a Water-Soluble Surfactant Composition in Need of Treatment

Water-Soluble Surfactant

As used herein "water-soluble surfactant" refers to those surfactants that are at least partially soluble in water, when measured at room temperature (25° C.). In one embodiment, the water-soluble surfactant is at least 10% soluble in water, alternatively is at least 20% soluble in water, still alternatively is at least 30% soluble in water, alternatively at least 40% soluble in water. As used herein in a relative sense, "water-soluble surfactant raw material" refers to the water-soluble surfactant itself, absent significant levels of water or undesirable by-products or starting materials such as those found in "water-soluble surfactant compositions" as described further below. Further, as used herein, "extracted water-soluble surfactant composition" or "treated water-soluble surfactant composition" refers to water-soluble surfactant compositions that have undergone the processes set forth herein and have some measurable level of reduction in undesirable non-polar materials versus the untreated water-soluble surfactant compositions.

As used herein, "in need of treatment" means that the water-soluble surfactant composition contains levels of undesirable non-polar materials higher than what is needed for a particular product usage. For oral care compositions, water-soluble surfactant compositions in need of treatment include those water-soluble surfactant compositions containing about 0.01% or more, by weight of the composition, of undesirable non-polar materials, alternatively containing more than about 0.1%, alternatively more than about 0.5%, alternatively more than about 0.7%, alternatively 1% or more, by weight of the composition, of such materials.

Identifying a Suitable Water-Soluble Surfactant

In one embodiment, the process herein includes the step of identifying a suitable water-soluble surfactant. The step of identifying a suitable water-soluble surfactant may include the sub-step of determining the surfactant's water solubility. When determining the surfactant's water solubility, conditions should be optimized for solubilizing the surfactant in water, as well as for minimizing the amount of the desirable raw material that could be extracted into the solvent phase along with the undesirable, relatively non-polar impurities. The pH may be adjusted so that charge will persist on suitable surfactants that are subject to ionization via pH manipulation in a typical pH range. Temperature can be raised, if needed, and samples should be vigorously shaken and/or stirred to facilitate formation of a homogenous solution. If a surfactant is aqueous soluble at roughly 10% or greater, then it is a good candidate for taste/odor/color cleanup by LLE to remove less-polar undesirable compounds.

To evaluate a surfactant, whose water solubility is in question, place 10 g solid surfactant into a glass vessel and add 100 mL of distilled, deionized water. Raise the temperature up to 60° C. (or higher if the melting point is higher), if needed, and shake, stir, or vortex, as appropriate, for up to 30 minutes. If all of the raw material is dissolved, creating a clear solution, then it is suitable for use in the processes set forth herein. For objective evaluation of solubility, after heating and stirring, vacuum filter through a membrane with 10 um pore size. Weigh solid material recovered on the filter to determine if a significant amount of surfactant remains undissolved. If needed for confirmation, utilize a direct analytical measure of the concentration of the material that is dissolved in the clear aqueous portion via appropriate analytical method.

Examples of water-soluble surfactants that may be purified by the processes herein include cocoamidopropyl betaines, lauryl betaines, capryl/capramidobetaines, sodium lauryl sulfates, mono alkyl phosphates, amine oxides, and mixtures thereof.

Water-soluble surfactants useful herein may, in some embodiments be selected from anionic surfactants such as alkyl phosphates. These surface active organophosphate agents have a strong affinity for enamel surface and have sufficient surface binding propensity to desorb pellicle proteins and remain affixed to enamel surfaces. Suitable examples of organophosphate compounds include mono-, di- or triesters represented by the general structure below wherein Z1, Z2, or Z3 may be identical or different, at least one being an organic moiety, in one embodiment selected from linear or branched, alkyl or alkenyl group of from 1 to 22 carbon atoms, optionally substituted by one or more phosphate groups; alkoxylated alkyl or alkenyl, (poly)saccharide, polyol or polyether group.

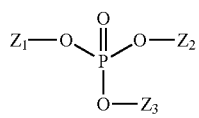

Some other agents include alkyl or alkenyl phosphate esters represented by the following structure:

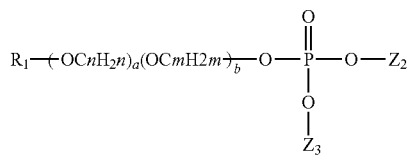

wherein R1 represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; Z2 and Z3 may be identical or different, each represents hydrogen, alkali metal, ammonium, protonated alkyl amine or protonated functional alkyl amine such as an alkanolamine, or a R1-(OCnH2n)a(OCmH2m)b- group. Examples of suitable agents include alkyl and alkyl(poly)alkoxy phosphates such as lauryl phosphate; PPGS ceteareth-10 phosphate; Laureth-1 phosphate; Laureth-3 phosphate; Laureth-9 phosphate; Trilaureth-4 phosphate; C12-18 PEG 9 phosphate; Sodium dilaureth-10 phosphate. In one embodiment, the alkyl phosphate is polymeric. Examples of polymeric alkyl phosphates include those containing repeating alkoxy groups as the polymeric portion, in particular 3 or more ethoxy, propoxy isopropoxy or butoxy groups.

Zwitterionic or amphoteric surfactants useful in the present invention include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate. Suitable amphoteric surfactants include betaine surfactants such as disclosed in U.S. Pat. No. 5,180,577 to Polefka et al. Typical alkyl dimethyl betaines include decyl betaine or 2-(N-decyl-N,N-dimethylammonio) acetate, coco betaine or 2-(N-coco-N,N-dimethyl ammonio) acetate, myristyl betaine, palmityl betaine, lauryl betaine, cetyl betaine, stearyl betaine, etc. The amidobetaines are exemplified by cocoamidoethyl betaine, cocamidopropyl betaine (CAPB), and lauramidopropyl betaine. The unwanted tastes often associated with these surfactants are soapy, bitter, chemical, and/or artificial.

Additional suitable polymeric organophosphate agents include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/PEG phosphate, dipropylene glycol phosphate, PEG glyceryl phosphate, PBG (polybutylene glycol) phosphate, PEG cyclodextrin phosphate, PEG sorbitan phosphate, PEG alkyl sorbitan phosphate, and PEG methyl glucoside phosphate. Suitable non-polymeric phosphates include alkyl mono glyceride phosphate, alkyl sorbitan phosphate, alkyl methyl glucoside phosphate, alkyl sucrose phosphates. The unwanted tastes often associated with these surfactants are soapy, chemical, and/or artificial.

Water-soluble amphoteric surfactants useful herein further include amine oxide surfactants Amine oxides are the result of oxidation of tertiary amines, typically C12-C18 alkyl dimethyl, N-oxides. For example, amine oxide surfactants useful herein may include lauryl dimethyl amine oxide; lauryl dihydroxyethyl amine oxide; cocamidopropyl amine oxide; Lauramidopropylamine oxide; cetyl dimethyl amine oxide; 3-Lauramidopropyl-N,N-dimethylamine oxide.

Water-soluble cationic surfactants useful in the present invention include derivatives of quaternary ammonium compounds having one long alkyl chain containing from about 8 to 18 carbon atoms such as lauryl trimethylammonium chloride; cetyl pyridinium chloride; cetyl trimethylammonium bromide; coconut alkyltrimethylammonium nitrite; cetyl pyridinium fluoride; etc. Preferred compounds are the quaternary ammonium halides having detergent properties described in U.S. Pat. No. 3,535,421 to Briner et al. Certain cationic surfactants can also act as germicides in the oral care compositions disclosed herein.

In another embodiment, the water-soluble surfactant is selected from anionic surfactants, zwitterionic surfactants, amphoteric surfactants, cationic surfactants, nonionic surfactants and mixtures thereof. In one embodiment, the water-soluble surfactant is selected from alkyl phosphate surfactants, alkyl phosphate ethoxylated surfactants, lauryl sulfate surfactants, betaine surfactants, betaine ethoxylated surfactants, amine oxide surfactants, and mixtures thereof. In another embodiment, the water-soluble surfactant is selected from alkyl phosphate surfactants, alkyl phosphate ethoxylated surfactants, and mixtures thereof. In one embodiment, the water-soluble surfactant is a mono alkyl phosphate surfactant.

In one embodiment, the surfactant is selected from cocoamidopropyl betaines, alkyl ethoxylated phosphates, mono alkyl phosphates, and mixtures thereof.

Water-Soluble Surfactant Composition

The water-soluble surfactant compositions disclosed herein contain a water-soluble surfactant and one or more undesirable non-polar materials. Water-soluble surfactant compositions useful herein include those commercially available from suppliers such as Rhodia (located in Spartanburg, S.C., USA), Stepan (located in Metamoros, Mexico and Winder, Ga., USA), Croda (located in Edison, N.J., USA) and Clariant (located in Charlotte, N.C., USA). Without being limited by theory, the presence of the undesirable non-polar materials are what present these compositions as being in need of treatment, e.g., the compositions are in need of removing such undesirable materials. Further without being limited by theory, it has been surprisingly found that current commercially available water-soluble surfactants, although purified to varying degrees by the manufacturers before sale, still contain significant amounts of undesirable non-polar materials that affect taste and/or color of the water-soluble surfactant raw material.

These undesirable non-polar materials may be unreacted starting materials used in the manufacturing of the surfactants (such as alcohol and/or amines), the products of side reactions occurring during the manufacturing process, or oxidation products (such as aldehydes).

The water-soluble surfactant composition may further comprise from about 0.1% to about 90% water, alternatively from about 10% to about 50%, by weight of the composition, of water. Typically water-soluble surfactants are commercially available as aqueous mixtures. The water may be removed in part or in whole from the water-soluble surfactant composition before conducting the liquid-liquid extraction processes of the present invention. Where the water is removed in large degree from the commercially available composition, it may be necessary to reintroduce water into the process as part of the extraction mixture.

Many commonly used water-soluble surfactant raw materials are produced by commercial suppliers as aqueous solutions at fairly high concentrations. These surfactants are good candidates for odor, color, and/or taste improvement by liquid-liquid extraction according to the processes set forth herein.

Water-soluble alkyl phosphate surfactant compositions that may be improved by the processes set forth herein include commercially available compositions shown in Table 1:

TABLE 1

| Supplier | Tradename | Alkyl | Chain | Concentration (in aqueous solution) | Salt | EO # | Average MW |
|---|---|---|---|---|---|---|---|
| Croda | 230K | Mono | Laureth | 40% | Potassium | 0 | 266.317 |
| Rhodia | L204K | Mono | Laureth | 20% | Potassium | 0 | 266.317 |
| Rhodia | L213/S | Mono | Laureth | 30% | Sodium | 1 | 310.3712 |
| Clariant | 340D | Di | Laureth | 40% | none | 4 | 442.5305 |
| Rhodia | L130 | Mono | Laureth | 100% | none | 3 | 398.4774 |
| Rhodia | L190 | Mono | Laureth | 100% | none | 9 | 662.7968 |

Undesirable Non-Polar Materials

As used herein "undesirable non-polar materials" refers generally to any non-polar materials that are found in the water-soluble surfactant composition in need of treatment. In one embodiment, the undesirable non-polar materials are selected from residual alcohols, alcohol ethoxylates, aldehydes, ethers, ketones, alkylamines, amides, and esters.

In one embodiment, the undesirable non-polar materials may be off-tasting components selected from impurities, unreacted starting materials, by-products and/or contaminants. Such undesirable non-polar materials may be described by consumers as soapy, bitter, metallic, earthy or dirty, and astringent. Soapy is typically characterized by the presence of dodecanal or dodecanol. Bitter taste may occur in the presence of alkyl amines or alcohols.

Extraction Mixture

In one step of the process herein, the water-soluble surfactant composition is contacted with an extraction solvent and water to form an extraction mixture comprising an aqueous phase and a solvent phase. In one embodiment, such as in a laboratory-scale batch process, the extraction mixture is then mixed vigorously for a period of from about 10 seconds to one minute. After mixing, the extraction mixture is allowed to rest for a period of from about 15 minutes to about 2 hours. Where multiple extractions are conducted in succession, the separation time may be shortened to a period of from about 10 to about 20 minutes.

In another embodiment, such as on an industrial scale, an industrial centrifuge extractor such as the BXP 190 manufactured by Rousselet Robatel may be used to take advantage of the density differences between two fluids to separate them via centrifugation. The devices can be operated in a countercurrent setup or as single stage extractions. Successive continuous extractions using an industrial centrifuge extractor can occur quite quickly, even in a matter of seconds, to reach the desired treated surfactant material.

The extraction mixture then contains the extraction solvent, surfactant and undesirable non-polar materials. In one embodiment, the extraction mixture comprises from about 10% to about 90%, by weight of the mixture, of water; from about 5% to about 60%, by weight of the mixture, of water-soluble surfactant; less than 5%, by weight of the mixture, of undesirable non-polar materials; and from about 10% to about 90%, by weight of the mixture, of solvent. In one embodiment, the ratio of extraction solvent to water-soluble surfactant in the extraction mixture is from about 1:10 to about 10:1, alternatively is from about 1:2 to about 2:1.

The water included in the extraction mixture may be provided in the water-soluble surfactant composition itself when obtained as an aqueous solution from the commercial supplier and/or may be water that is added during the extraction process. In some instances, the water level in a water-soluble surfactant aqueous solution may be reduced before contacting the water-soluble surfactant composition with the extraction solvent to reduce the level of solvent needed for the processes herein.

In one embodiment, the extraction mixture further comprises a phase separation enhancer selected from salts, pH modifiers, and mixtures thereof.

In one embodiment, after the extraction mixture is formed and contains both an aqueous phase and a solvent phase, the aqueous phase is then separated from the solvent phase. In another embodiment, after the two phases are separated, the extraction solvent is recovered from the solvent phase and reused in subsequent liquid-liquid extraction processes.

In one embodiment, during the step of separating the aqueous phase from the solvent, the temperature is adjusted to improve the extraction efficiency. As used herein, "extraction efficiency" refers to the ability of the process to remove undesirable impurities from the water-soluble surfactant composition in need of treatment.

In one embodiment, during the process, the pressure under which the process takes place is adjusted to improve the extraction efficiency.

In one embodiment, the process steps herein are repeated in succession until the desired amount of undesirable non-polar impurities is removed. In one embodiment, the treated water-soluble surfactant composition is collected and the process steps are repeated at least two times, alternatively at least 3 times, still alternatively at least 4 times in succession, each time further reducing the level of undesirable water-soluble impurities.

In another embodiment, multiple extractions are performed in series after removal of the extraction solvent from preceding extraction.

As used herein, the terms "extract" and "extraction" refer to the process of removing undesirable components from the desirable components of the water-soluble surfactant composition. The undesirable components could be associated with microorganism removal and/or other impurity or contaminant removal, primarily via preferential solubility in the extraction solvent.

As used herein, the terms "removal", "reduce", "reduction", and their derivatives refer to partial reduction of the number or concentration of undesirable materials and may be considered in a relative sense, particularly when multiple repetitions of the process steps herein are used in succession on the same starting material.

Extraction Solvent

As used herein, "extraction solvent" refers to any liquid or supercritical fluid that can be used to solubilize undesirable non-polar materials that are contained within a water-soluble surfactant composition. Organic solvents with acceptable safety profiles that will form a liquid bilayer with aqueous surfactants could be used either alone or in combination with other solvents such as ethyl acetate, ethanol, propylene glycol, PEGs, other ethers or esters, or other solvents, etc. to achieve a similar result. One example of a useful supercritical fluid is carbon dioxide. A range of ratios of solvent to surfactant, a range of surfactant concentrations, the mixing and/or extraction conditions, etc. are variables that could be optimized for a particular application of this general approach.

Without being limited by theory, when thorough chemical composition data on the undesirable non-polar materials found in the water-soluble surfactant composition in need of treatment are obtained through in-depth chemical characterization and are well-understood, an investigation can be initiated to determine if the impurities are primarily responsible for malodors and off-tastes, or if the surfactants themselves are contributing a large fraction of the malodors and off tastes.

Extraction solvents useful herein include those having individual Hansen solubility parameters of a dispersion force component ($\delta_D$) ranging from about 15 to about 17 (MPa)$^{0.5}$, a polar component ($\delta_P$) ranging from 0 to about 9 (MPa)$^{0.5}$ and a hydrogen bonding component ($\delta_H$) ranging from 0 to about 11 (MPa)$^{0.5}$.

In one embodiment, the solvent has individual Hansen solubility parameters of a dispersion force component ($\delta_D$) ranging from about 13 to about 19 (MPa)$^{0.5}$, a polar component ($\delta_P$) ranging from about 2 to about 9 (MPa)$^{0.5}$ and a hydrogen bonding component ($\delta_H$) ranging from about 2 to about 11 (MPa)$^{0.5}$. In one embodiment, the polar component ranges from about 4 to about 6, in another embodiment, the hydrogen bonding component ranges from about 6 to about 9.

In addition to Hansen solubility parameters, the solvent will form distinct layers when combined with water and the water-soluble surfactant composition. In order to quickly determine whether a solvent will meet this criteria, the following visual separation test may be used: using a 30 ml glass vial, add 10 mL of the proposed extraction solvent, 10 mL of a 30% aqueous solution of the water-soluble surfactant composition, cap the vial, shake vigorously for 30 seconds, allow to rest for 30 minutes, visually inspect for visible precipitation and two distinct aqueous layers. If there is no visible precipitation and at least two distinct layers are formed, the solvent passes the visual separation test and may be used as an extraction solvent according to the processes set forth herein.

In one embodiment, the extraction solvents useful herein have a log P value of greater than 0.5.

Extraction solvents useful herein include ethyl acetate, water-saturated ethyl acetate, ethyl propionate, ethyl butyrate, ethyl pentanoate, ethyl caproate, ethyl caprylate, ethyl pelargonate methyl acetate, methyl propionate, methyl butyrate, short chain esters and mixtures thereof. In one embodiment, the extraction solvent is selected from food grade ethyl esters.

In one embodiment, the extraction solvent is substantially free of (i.e. comprises no reasonably measurable quantity of) ethyl lactate, alternatively contains less than 0.0001% of ethyl lactate.

Other extraction solvents useful herein include ketones such as methyl ethyl ketone, ethers such as di-n-propyl ether, lactones, acetals, and mixtures thereof.

Other extraction solvents useful herein include those selected from hexane, cyclohexane, heptane, chloroform, toluene, methylene chloride, methyl nonafluoroether, ethyl nonafluoroether, carbon tetrachloride, and mixtures thereof. HFE 7100, HFE 7200, and HFE 7500 are tradenames of commercially available hydrofluoroethers available from TCI AMERICA, 9211 N. Harborgate Street, Portland, Oreg. 97203, U.S.A.

Mixtures of extraction solvents may also be used.

In one embodiment, the extraction mixture is substantially free of (i.e. comprises no reasonably measurable quantity of) THF.

In one embodiment, the extraction mixture comprises mono alkyl phosphate and is substantially free of (i.e. comprises no reasonably measurable quantity of) 1-octanol and phenoxy ethanol.

Extraction solvents useful herein also include supercritical fluids such as carbon dioxide. As used herein, "supercritical carbon dioxide" is carbon dioxide that is at a temperature and a pressure greater than Tr=1 and Pr=1. Tr is T/Tc where T is the present temperature of the supercritical carbon dioxide and Tc is the critical temperature. Pr is P/Pc where P is the present pressure of the supercritical carbon dioxide and Pc is the critical pressure. Tc, the critical temperature for carbon dioxide ($CO_2$), is 31.1 degrees Celsius (deg. C.), or 304.1 degrees Kelvin (K), and Pc is 73 atmospheres (atm) or about 1073 pounds per square inch (PSI).

In more general terms, supercritical carbon dioxide refers to carbon dioxide that is in a fluid state while also being at or above both its critical temperature and pressure. Carbon dioxide usually behaves as a gas in air at standard temperature and pressure (STP) or as a solid called dry ice when frozen. If the temperature and pressure are both increased from standard temperature and pressure to be at or above the critical point for carbon dioxide, it can adopt properties midway between a gas and a liquid. More specifically, it behaves as a supercritical fluid above its critical temperature (31.1 deg. C.) and critical pressure (73 atm), expanding to fill its container like a gas but with a density like that of a liquid. The supercritical fluid region of the phase diagram is defined as a temperature above the critical temperature (31.1 deg. C.) to a pressure above the critical pressure (73.8 bar or 1070 PSI).

When using a supercritical fluid as the extraction solvent, it is possible to choose a "batch-type" system or choose a "continuous-type" system. The batch systems can be used in parallel or in series, operated on a cyclic basis (at prescribed residence times), be sequentially loaded, processed, and unloaded, and yield a sufficient bulk removal efficiency. The "continuous-type" systems generally refer to a number of batch vessels, operated sequentially, with the supercritical carbon dioxide gas flow and the sequential loading, processing, and unloading of the feed and product solids can be envisioned as counter current flow of the solids movement from feed to product with respect to the flow of the supercritical carbon dioxide. The directional loading, processing, and unloading is opposite to the flow of the supercritical carbon dioxide. This type of "continuous", counter current operation is generally referred to as continuous, counter current, sequencing-batch operation. Therefore, when there are one or two batch stages, in series or parallel, the term "batch" tends to be used, and when there are three or more stages, if they operate in parallel flow to the supercritical carbon dioxide, the term "batch" is also used. However, when they operate in counter current flow of the material to be extracted to the supercritical carbon dioxide, we call them counter current "sequencing-batch" simulating counter current flows of material feed and desired product to the flow direction of the supercritical carbon dioxide. It should be understood that "continuous" can also define a process in which the feed and solvent are fed continuously through a fixed system and the products are continuously removed.

When the supercritical fluid is selected as the extraction solvent, the separation of the aqueous phase from the solvent phase may occur by releasing the temperature and pressure placed upon the supercritical fluid, allowing the fluid to return to a gaseous state.

Selection of an Extraction Solvent

In one embodiment, the process further comprises a step of selecting an extraction solvent suitable for use with the water-soluble surfactant in need of treatment.

Such step includes evaluating the extraction solvent under consideration with the water-soluble surfactant in need of treatment. Evaluation of the solvent includes combining the proposed solvent with the water-soluble surfactant composition in need of treatment to determine whether the solvent forms a 2-phase system with the surfactant water mixture. The pH, temperature, or ionic strength may be adjusted to deliver a good two-phase break, and also to optimize the extraction efficiency. The extraction solvent should not cause significant precipitation when combined with the water/surfactant mixture. Since a successful two-phase separation will be achieved with suitable extraction solvents, the solvent polarity is expected to preferentially extract non-polar impurities into the extraction solvent layer and away from the aqueous surfactant phase. In one embodiment, the solvent will be food grade and easily separable from the aqueous/surfactant phase. Selection of a solvent that is easily recoverable from the extracted impurities is also desirable, i.e. by fractional distillation, so that it can be re-used for subsequent extractions.

The solvents selected for the solubilization method of this invention are based upon solubility parameters and cohesion properties explained by Charles Hansen in "Hansen Solubility Parameters: A User's Handbook" by Charles M. Hansen, CRC Press (2007) and in "The CRC Handbook and Solubility Parameters and Cohesion Parameters," Edited by Allan F. M. Barton (1999). Each material is defined by three points in 3D space and these three points are known as the Hansen Solubility Parameters (HSP) which may be defined as follows.

Solubility parameters are theoretically calculated numerical constants which are a useful tool in predicting the ability of a solvent material to dissolve a particular solute. When the solubility parameters of a solvent falls within the solubility parameter range of a solute, i.e., the material to be dissolved, solubilization of the solute is likely to occur. There are three Hansen empirically- and theoretically-derived solubility parameters, a dispersion-force component ($\delta_D$), a polar or dipole interaction component ($\delta_P$) and a hydrogen-bonding component ($\delta_H$). Each of the three parameters (i.e., dispersion, polar and hydrogen bonding) represents a different characteristic of solvency, or solvent capability. In combination, the three parameters are a measure of the overall strength and selectivity of a solvent. The Total Hansen solubility parameter, which is the square root of the sum of the squares of the three parameters mentioned previously, provides a more general description of the solvency of the solvents. Individual and total Solubility Parameter units are given in $MPa^{0.5}$ or $(J/cc)^{0.5}$.

These three parameters can be treated as co-ordinates for a point in three dimensions also known as the Hansen space. The nearer two molecules are in this three dimensional space, the more likely they are to dissolve into each other. To determine if the parameters of two molecules (usually a solvent and a polymer) are within range a value called interaction radius ($R_O$) is given to the substance being dissolved. This value determines the radius of the sphere in Hansen space and its center is the three Hansen parameters. To calculate the distance (Ra) between Hansen parameters in Hansen space the following formula is used.

$$(Ru)^2 = 4(\delta_{d2}-\delta_{d1})^2 + (\delta_{p2}-\delta_{p1})^2 + (\delta_{h2}-\delta_{h1})^2$$

The Hansen solubility parameters can be calculated by "Molecular Modeling Pro" software, version 5.1.9 (ChemSW, Fairfield Calif., www.chemsw.com) or Hansen Solubility from Dynacomp Software. The solubility parameters of solvents useful herein are shown in Table 1, below.

TABLE 1

| Component | Dispersion ($\delta D$) | Polarity ($\delta P$) | Hydrogen Bonding ($\delta H$) | Ra (With Ethyl Acetate) | Ra (With Dodecanol) |
|---|---|---|---|---|---|
| ethyl acetate | 15.8 | 5.3 | 7.2 | 0 | 4.5 |
| Carbon Dioxide | 15.7 | 6.3 | 5.7 | 1.8 | 5.7 |
| hexane | 14.9 | 0 | 0 | 9.1 | 10.0 |
| heptanes | 15.3 | 0 | 0 | 9 | 10.2 |
| benzene | 18.4 | 0 | 2 | 9.1 | 11.8 |
| diethyl ether | 14.5 | 2.9 | 5.1 | 4.1 | 4.3 |
| di-n-propyl ether | 15.5 | 2.3 | 4.5 | 4.1 | 5.7 |
| methylene chloride | 18.2 | 6.3 | 6.1 | 5 | 9.4 |
| carbon tetrachloride | 17.8 | 0 | 0.6 | 9.4 | 12.0 |
| propylene Carbonate | 20 | 18 | 4.1 | 15.5 | 19.6 |
| propylene glycol methyl ether acetate | 15.6 | 5.6 | 9.8 | 2.6 | 3.9 |
| 1,1,1-trichloroethane | 16.8 | 4.3 | 2 | 5.7 | 9.2 |
| methyl nonafluorobutyl ether* | 13.74 | 3.59 | 4.14 | 5.4 | 5.2 |
| ethyl nonafluorobutyl ether* | 14.31 | 4.36 | 3.98 | 4.5 | 5.5 |

*Methyl and Ethyl Nonafluorobutyl Ethers are commercially available from TCI AMERICA, 9211 N. Harborgate Street, Portland, OR 97203, U.S.A.

Aqueous Phase

As used herein, "aqueous phase" refers to the portion of the extraction mixture containing water, water-soluble surfactant, and other water-soluble materials.

In one embodiment, the processes of the present invention may further include a step of adjusting the ionic strength of the aqueous phase up or down to improve the extraction efficiency.

Solvent Phase

As used herein, "solvent phase" refers to the portion of the extraction mixture containing the extraction solvent, the undesirable non-polar materials, and other water-insoluble materials.

Generally, the solvent phase and the aqueous phase will be immiscible.

In one embodiment, after separation of the aqueous and solvent phases, the aqueous phase still contains small amounts of the extraction solvent and the extraction solvent may be further removed from the aqueous phase by subsequent extraction steps, evaporation (such as with a rotavapor or open-air, optionally with a nitrogen stream) or combinations thereof.

Separating the Aqueous Phase from the Solvent Phase

As discussed more fully above, the separation of the aqueous phase from the solvent phase may occur using traditional liquid-liquid extraction techniques. Such separation may be crudely done based upon the phase break, particularly where multiple rounds of extraction are planned. On a lab bench or pilot plant scale this may mean by use of a separatory funnel, while on an industrial scale, this may mean by use of standard equipment for centrifugation and separation in a continuous process or in very large tanks equipped for separation on a batch basis.

In one embodiment, the step of separating the aqueous phase from the solvent phase further comprises centrifuging the extraction mixture.

In one embodiment, the extraction mixture is mixed for from about 10 seconds to about one minute with vigorous mixing and at ambient temperature before allowing the mixture to settle into two phases and separating the aqueous phase from the solvent phase.

In one embodiment, the step of separating the aqueous phase from the solvent phase comprises reducing the heat and pressure applied to a supercritical fluid, such as carbon dioxide, allowing the supercritical fluid to return to a gaseous state, and allowing the gas to escape from the extraction mixture.

The process may further comprise the step of removing any residual solvent from the aqueous phase. In one embodiment the step of removing any residual solvent from the aqueous phase includes the use of an industrial method selected from vacuum stripping (with or without heat), fractional distillation, wiped-film evaporation, carbon filtration, or combinations thereof.

Recovering the Treated Water-Soluble Surfactant

The processes according to the present invention may further include a step of recovering the treated water-soluble surfactant composition from the aqueous phase by evaporation or other traditional means.

In one embodiment, the treated water-soluble surfactant composition contains from about 10% to about 50%, alternatively from about 20% to about 30% of the treated water-soluble surfactant, from about 60 to about 90%, alternatively from about 70% to about 80% water, and 1% or less, alternatively 0.7% or less, alternatively 0.5% or less, alternatively 0.1% or less, alternatively 0.05% or less, alternatively 0.01% or less, of undesirable non-polar materials, all by weight of the treated composition.

In one embodiment, the treated mono alkyl phosphate surfactant composition contains 0.7% or less, alternatively 0.5% or less, alternatively 0.1% or less, alternatively 0.05% or less, alternatively 0.01% or less, by weight of the treated composition, of undesirable non-polar materials.

In one embodiment, the treated cocoamidopropyl betaine surfactant composition contains 0.1% or less, alternatively 0.07% or less, alternatively 0.05% or less, alternatively 0.01% or less, alternatively 0.005% or less, 0.0001% or less, alternatively no measurable quantity, by weight of the treated composition, of amine and amide materials.

In one embodiment, the treated cocoamidopropyl betaine surfactant composition contains at least 20% cocoamidopropyl betaine surfactant and 10 ppm or less, alternatively 5 ppm or less, alternatively 1 ppm or less, alternatively 500 ppb or less, alternatively no measurable quantity, by weight of the treated composition, of amine and amide materials.

In one embodiment, the treated cocoamidopropyl betaine surfactant composition contains 0.1% or less, alternatively 0.07% or less, alternatively 0.05% or less, alternatively 0.01% or less, alternatively 0.005% or less, 0.0001% or less, alternatively no measurable quantity, by weight of the treated composition, of undesirable non-polar materials.

In one embodiment, the treated water-soluble surfactant composition contains from about 10% to about 50%, alternatively from about 20% to about 30% of the treated water-soluble surfactant, from about 60 to about 90%, alternatively from about 70% to about 80% water, and 1% or less of total alcohols, all by weight of the treated composition.

In one embodiment, the treated mono alkyl phosphate surfactant composition contains 0.7% or less, alternatively 0.5% or less, alternatively 0.1% or less, alternatively 0.05% or less, alternatively 0.01% or less, by weight of the treated composition, of total alcohols.

Recycling the Solvent

In one embodiment, the process further includes a step of separating the extraction solvent from the solvent phase and optionally reusing the extraction solvent for further liquid-liquid extraction processes.

In one embodiment, the step of recycling the solvent includes the use of a fractionating column (or distillation tower). Fractionating columns have been shown capable of separating these types of streams and removing them for varying uses. An example process that incorporates a fractionating column step is shown in FIG. 1. Design of the fractionating column will need to take into account the potential markets for the varying fractions, throughput needs for the system, and overall costs. The size and number of plates used in the distillation tower may be selected with these factors in mind.

A fractionating column or fractionation column may be used in the distillation of liquid mixtures so as to separate the mixture into its component parts, or fractions, based on the differences in their volatilities. Fractionating columns may vary in size and are used in small scale laboratory distillations as well as for large-scale industrial distillations.

Fractionating columns help to separate the mixture by allowing the mixed vapors to cool, condense, and vaporize again in accordance with Raoult's law. With each condensation-vaporization cycle, the vapors are enriched in a certain component.

In a typical fractional distillation, a liquid mixture is heated in the distilling flask, and the resulting vapor rises up the fractionating column. The vapor condenses on glass spurs (known as trays or plates) inside the column, and returns to the distilling flask, refluxing the rising distillate vapor. The hottest tray is at the bottom of the column and the coolest tray is at the top. At steady-state conditions, the vapor and liquid on each tray reach an equilibrium. Only the most volatile of the vapors stays in gas form all the way to the top, where it may then proceed through a condenser, which cools the vapor until it condenses into a liquid distillate. The separation may be enhanced by the addition of more trays (to a practical limitation of heat, flow, etc.).

Fractional distillation is one of the unit operations of chemical engineering. Fractionating columns are widely used in the chemical process industries where large quantities of liquids have to be distilled. Many fractions can be recovered through this method and for industrial processes, the limitation is typically only product requirements and economics.

Industrial distillation is typically performed in large, vertical cylindrical columns known as "distillation towers" or "distillation columns" with diameters ranging from about 65 centimeters to 6 meters and heights ranging from about 6 meters to 60 meters or more. Industrial distillation towers are usually operated at a continuous steady state. Unless disturbed by changes in feed, heat, ambient temperature, or condensing, the amount of feed being added normally equals the amount of product being removed.

Other means of recycling the solvent phase include use of a cyclone separator. It may be possible to use the density differences of the materials in the solvent phase to drive their separation. This approach has the advantage of typically being more economical to install and operate, but may reduce the degree of separation that can be achieved versus a distillation approach.

Preparing a Solid Water-Soluble Surfactant

In one embodiment, the process further comprises the step of heating a solid impure surfactant material to its melting point. In one embodiment, heating the solid impure surfactant material to a temperature of from about 25° C. to about 80° C., alternatively from about 30° C. to about 60° C. before the step of contacting with an extraction solvent and water.

Incorporating into Oral Care Compositions

The processes of the present invention may further include a step of incorporating the treated water-soluble surfactant composition into an oral care composition.

Oral Care Compositions

The treated water-soluble surfactant compositions resulting from the processes according to the present invention, may, in one embodiment, be incorporated into an oral care composition having improved taste vs. a water-soluble surfactant untreated by the processes set forth herein.

As used herein, "oral care composition" is meant a product, which in the ordinary course of usage, is not intentionally swallowed for purposes of systemic administration of particular therapeutic agents, but rather is retained in the oral cavity for a time sufficient to contact substantially all of the dental surfaces and/or oral tissues for purposes of oral activity. The oral care composition may be in various forms including toothpaste, dentifrice, tooth gel, subgingival gel, mouthrinse, mousse, foam, mouthspray, lozenge, chewable tablet, chewing gum or denture product. The oral care composition may also be incorporated onto strips or films for direct application or attachment to oral surfaces.

Procedure for Assessing Extraction Efficacy

In one embodiment, in conjunction with the processes according to the present invention, a step of assessing extraction efficacy is performed on the water-soluble surfactant composition. Such as step may be performed as follows:

1. Supply a water-soluble surfactant composition.
2. To the water-soluble surfactant composition, add the extraction solvent, such as ethyl acetate, all in a separatory funnel.
3. Mix vigorously by shaking the separatory funnel for approximately 1 minute and then allow the liquid layers to separate.
4. Collect the aqueous layer containing the desirable water-soluble surfactant.
5. Separately collect the solvent layer containing the undesirable materials and either discard or utilize the solvent and undesirable materials for other purposes. For example, if the undesirable materials are starting materials in the water-soluble surfactant manufacture, they could be isolated and re-used to make more surfactant. The extraction solvent could be purified for later re-use in the extraction procedure.
6. Analyze samples from both the pre- and post-extracted oral care component via immersion Solid Phase Microextraction (SPME) (or LLE) followed by GC-MS (using an Agilent model 6890 GC & model 5973 Mass Spectrometric Detector, Agilent Technologies, Wilmington, Del., USA). Compare the impurity levels in the pre- and post-extracted samples to determine the efficiency of their removal.
7. Smell and/or taste the pre- and post-extracted material directly or after spiking into an Oral Care product to sensorially dimension the level of improvement.

EXAMPLES

Example I

Improved MAP L213/S Surfactant

Undesirable non-polar materials were extracted from MAP L213/S (a mono alkyl phosphate surfactant in aqueous solution, see Table 1 above), supplied by Rhodia, using the processes set forth herein wherein ethyl acetate (supplied by Honeywell Burdick & Jackson, Muskegon, Mich., USA) was used as the extraction solvent. The extracted materials were then analyzed and the treated MAP L213/S was evaluated for taste and odor after the extraction and shown to be very mild, especially when compared with the starting MAP L213/S material. The undesirable materials removed from the ML213/S commercially supplied material are set forth in Table 3, below. The following process steps were taken:

1. 100 grams of MAP L213/S were placed into a clean 250 mL separatory funnel.

2. 100 mL of ethyl acetate was added to the separatory funnel, which was stoppered, and shaken vigorously for approximately 1 minute.

3. The separatory funnel contents were then rested for a period of time until they settled into two visibly distinct layers.

4. The bottom layer (treated MAP L213/S) was drained from the separatory funnel into a second, clean 250 mL separatory funnel.

5. The ethyl acetate was separately collected and set aside for other purposes.

6. A second aliquot of 100 mL of fresh ethyl acetate was then added to the treated MAP L213/S in the separatory funnel and the steps 2-5 were repeated for a total of 5 times.

7. After the last extraction step, the aqueous layer was collected into a round bottom flask, which was then placed on a rotavapor (model RE111 supplied by BUCHI Labortechnik AG in Flawil, Switzerland). The water bath of the rotavapor was set at 80° C. and allowed to run until the ethyl acetate odor is no longer perceived.

7. The mass of the treated MAP L213/S surfactant was then obtained and water was added to make up for any mass loss due to water loss along with the EtOAc removal.

TABLE 3

Results of Mono alkyl phosphate LLE treatment with EtOAc

| Undesirable Material | Retention Time (Min) | Control (Pre-extract) Peak Area | Post Extract Peak Area | Area Reduction (%) |
|---|---|---|---|---|
| Undecane | 3.39 | 1216114 | 0 | 100.0 |
| Dodecene Isomer | 4.35 | 3218343 | 0 | 100.0 |
| Dodecene Isomer | 4.42 | 3450618 | 0 | 100.0 |
| Dodecene Isomer | 4.46 | 2311369 | 0 | 100.0 |
| Dodecene Isomer | 4.57 | 4329376 | 0 | 100.0 |
| Dodecene Isomer | 4.66 | 2547216 | 0 | 100.0 |
| Tridecene Isomer | 5.09 | 2406145 | 0 | 100.0 |
| Tridecene Isomer | 5.15 | 1220445 | 0 | 100.0 |
| Tridecene Isomer | 5.19 | 438095 | 0 | 100.0 |
| Tridecene Isomer | 5.29 | 1367495 | 0 | 100.0 |
| Tridecene Isomer | 5.38 | 1114436 | 0 | 100.0 |
| Tetradecene Isomer | 5.45 | 674727 | 0 | 100.0 |
| Tetradecene Isomer | 5.52 | 1030783 | 0 | 100.0 |
| Tetradecene Isomer | 5.59 | 1218184 | 0 | 100.0 |
| Tetradecene Isomer | 5.63 | 1589820 | 0 | 100.0 |
| Tetradecene Isomer | 5.77 | 573418 | 0 | 100.0 |
| Tetradecene Isomer | 5.80 | 220422 | 0 | 100.0 |
| Tetradecene Isomer | 5.83 | 184627 | 0 | 100.0 |
| Tetradecene Isomer | 5.88 | 300141 | 0 | 100.0 |
| Tetradecene Isomer | 5.97 | 199647 | 0 | 100.0 |
| Tetradecene Isomer | 5.99 | 175759 | 0 | 100.0 |
| Tetradecene Isomer | 6.06 | 177721 | 0 | 100.0 |
| Pentadecane | 6.22 | 669888 | 0 | 100.0 |
| Methyl 4,6-decadienyl ether | 6.61 | 1023628 | 0 | 100.0 |
| Hexadecane | 6.83 | 1645290 | 0 | 100.0 |
| Dodecanal | 7.57 | 2654710 | 129439 | 95.1 |
| Unknown | 7.60 | 776038 | 0 | 100.0 |
| Unknown | 7.64 | 1108611 | 0 | 100.0 |
| Unknown | 7.70 | 1879031 | 0 | 100.0 |
| Methyl 6,8-dodecadienyl ether | 7.80 | 1223734 | 0 | 100.0 |
| Unknown | 7.84 | 1463962 | 0 | 100.0 |
| Unknown | 7.95 | 3115904 | 0 | 100.0 |
| Butyl-substituted tetrahydrofuran | 8.04 | 5371992 | 0 | 100.0 |
| Branched alcohol | 8.29 | 1323195 | 0 | 100.0 |
| Branched alcohols | 8.38 | 4633193 | 0 | 100.0 |
| Branched alcohols | 8.48 | 8500950 | 0 | 100.0 |
| Dodecanol | 8.88 | 101956289 | 932638 | 99.1 |
| Ethylene glycol monododecyl ether | 10.23 | 55816598 | 522217 | 99.1 |
| Diethylene glycol monododecyl ether | 12.00 | 31588284 | 560933 | 98.2 |
| Triethylene glycol monododecyl ether | 14.90 | 8518697 | 264967 | 96.9 |
| | | | Average % Reduction | 99.7 |

The resulting treated MAP L213/S was then subjected to comparative taste testing as follows:

The following MAP L213/S compounds (all based upon the MAP L213/S surfactant commercially available from Rhodia) were subjected to a 6 person panel for tasting. Each MAP material was diluted to a level of 1% surfactant in distilled water and neutralized to pH 7. 10 mL samples were provided in 15 mL cups to the panelists. Panelists were instructed to not sample materials more often than once in the morning and once in the afternoon in order to provide enough time for the palate to clear between samples and were instructed to not eat or drink within 15 minutes before sampling. The panelist was instructed to empty the contents of the cup into their mouth without swallowing, swish the product for 10-20 seconds, expectorate, wait 10-20 seconds, and then rate their perceptions for the following categories on a scale of 0 to 60:1) soapy taste; 2) bitterness amount; 3) other off-taste amount; 4) "soapy taste" intensity; 5) "bitter taste" intensity.

176=Rhodia L213/S, lot SW10G-4636 251=Rhodia L213/S, lot 012
389=Rhodia L213/S, lot 010
462=Rhodia L213/S, lot 011
937=Rhodia L213/S, lot 001 extracted with ethyl acetate pursuant to the process steps set forth above in this Example I
Control=Rhodia L213/S, lot 001

As may be seen in Table 4, the control and the comparative examples 176, 251, 389, and 462, all had significantly higher ratings for negative taste elements such as the soapy taste, bitterness amount, other off-taste amount, soapy taste intensity, and bitter taste intensity than the MAP composition treated with ethyl acetate according to the processes set forth herein.

TABLE 4

| | Attribute n = 6 | | | | | |
|---|---|---|---|---|---|---|
| | CTL | 176 (Comp) | 251 (Comp) | 389 (Comp) | 462 (Comp) | 937 (Example I) |
| Soapy Taste | 41.25 | 47.50 | 33.75 | 30.42 | 38.75 | 12.50 |
| Bitterness Amount | 32.50 | 44.08 | 42.08 | 39.58 | 44.58 | 5.83 |
| Other Off-taste Amount | 32.50 | 34.00 | 24.58 | 26.25 | 26.08 | 3.75 |
| "Soapy Taste" Intensity | 42.08 | 45.00 | 32.00 | 28.75 | 39.25 | 7.50 |
| "Bitter Taste" Intensity | 31.25 | 39.17 | 41.25 | 38.75 | 42.92 | 3.17 |

Example II

Improved Cocoamidopropyl Betaine Surfactant

Undesirable non-polar materials were extracted from cocoamidopropyl betaine surfactant, supplied by Stepan, Mexico SA DE CV (Matamoros, MX), using the process steps shown in Example I, except that 20 grams cocoamidopropyl betaine and 20 mL of solvent were used (in place of 100 grams of MAP and 100 mL of solvent) and only 3 repetitions (stages) of steps 2 through 5—substituting the cocoamidopropyl betaine for the MAP L213/S. The extracted materials were then analyzed and the treated cocoamidopropyl betaine surfactant was evaluated for taste and odor after the extraction and shown to be very mild, especially when compared with the starting material. The undesirable materials removed from the commercially supplied material are set forth in Table 5, below.

TABLE 5

Cocoamidopropyl Betaine - Pre and Post 3 Stages of EtOAc Extraction

| Impurity | Retention Time (Min) | Control (Pre-extract) Peak Area | Post Extract Peak Area | Area Reduction (%) |
|---|---|---|---|---|
| Cyclohexyl benzene | 7.43 | 421510 | 0 | 100.0 |
| Dodecanal | 7.57 | 2718310 | 91634 | 96.6 |

TABLE 5-continued

Cocoamidopropyl Betaine - Pre and Post 3 Stages of EtOAc Extraction

| Impurity | Retention Time (Min) | Control (Pre-extract) Peak Area | Post Extract Peak Area | Area Reduction (%) |
|---|---|---|---|---|
| Methyl dodecanoate | 8.04 | 3597403 | 12025 | 99.7 |
| Benzyl alcohol | 8.52 | 11186150 | 370371 | 96.7 |
| Tetradecanal | 8.70 | 396280 | 0 | 100.0 |
| Dodecanol | 8.87 | 1590140 | 319173 | 79.9 |
| Methyl tetradecanoate | 9.11 | 515756 | 0 | 100.0 |
| Biphenyl | 9.19 | 2524375 | 0 | 100.0 |
| Diphenyl ether | 9.28 | 8312954 | 0 | 100.0 |
| Tetradecanol | 9.86 | 264984 | 0 | 100.0 |
| Unknown | 10.16 | 1794756 | 570477 | 68.2 |
| N,N-Dimethyldodecanamide | 10.85 | 737881 | 0 | 100.0 |
| Benzoic Acid | 11.13 | 627445 | 70858 | 88.7 |
| Dodecanoic acid | 11.23 | 7295585 | 295959 | 95.9 |
| N,N-Dimethylpalmitamide | 11.83 | 300264 | 0 | 100.0 |
| Tetradecanoic acid | 12.26 | 2070533 | 93129 | 95.5 |
| Dodecanamide | 12.80 | 378693 | 0 | 100.0 |
| Unknown | 13.66 | 948057 | 515784 | 45.6 |
| Tertiary alkyl dimethylamine | 14.26 | 1761483 | 495040 | 71.9 |
| | | | Average % Reduction | 91.5 |

Example III

Improved Lauryl Betaine Surfactant

Undesirable non-polar materials were extracted from lauryl betaine surfactant, supplied by Mason Chemical Company (Arlington Heights, Ill., USA), using the process steps shown in Example I, substituting the lauryl betaine for the MAP L213/S and only four repetitions of steps (stages) 2 through 5 were completed. The extracted materials were then analyzed and the treated lauryl betaine surfactant was evaluated for taste and odor after the extraction and shown to be very mild, especially when compared with the starting material. The undesirable materials removed from the commercially supplied material are set forth in Table 6, below.

TABLE 6

Lauryl Betaine - Pre and Post 4 Stages of EtOAc Extraction

| Impurity | Retention Time (Min) | Control (Pre-extract) Peak Area | Post Extract Peak Area | Area Reduction (%) |
|---|---|---|---|---|
| Dodecene Isomer | 4.14 | 268607 | 0 | 100.0 |
| Dodecene Isomer | 4.25 | 269099 | 0 | 100.0 |
| Dodecene Isomer | 4.36 | 100143 | 0 | 100.0 |
| Dodecene Isomer | 4.42 | 249301 | 0 | 100.0 |
| Dodecene Isomer | 4.51 | 210691 | 0 | 100.0 |
| Dodecene Isomer | 4.61 | 533604 | 0 | 100.0 |
| Dodecene Isomer | 4.68 | 77816 | 0 | 100.0 |
| Tertiary Alkyl Dimethyl amine | 5.83 | 119401 | 0 | 100.0 |
| Tertiary Alkyl Dimethyl amine | 6.11 | 110815 | 0 | 100.0 |
| 2-Ethyl-1-hexanol | 6.18 | 197861 | 0 | 100.0 |
| N,N-Dimethyl-1-dodecanamine | 7.05 | 12603358 | 1716473 | 86.4 |
| | | | Average % Reduction | 98.8 |

Example IV

Improved Sodium Lauryl Sulfate Surfactant

Undesirable non-polar materials were extracted from sodium lauryl sulfate surfactant, supplied by Stepan (Winder, Ga., USA), using the process steps shown in Example I, substituting the sodium lauryl sulfate for the MAP L213/S and only three repetitions (stages) of steps 2 through 5 were completed. The extracted materials were then analyzed and the treated sodium lauryl sulfate surfactant was evaluated for taste and odor after the extraction and shown to be very mild, especially when compared with the starting material. The undesirable materials removed from the commercially supplied material are set forth in Table 7, below.

TABLE 7

SODIUM LAURYL SULFATE - Pre and Post 3 Stages of EtOAc Extraction

| Impurity | Retention Time (Min) | Control (Pre-extract) Peak Area | Post Extract Peak Area | Area Reduction (%) |
|---|---|---|---|---|
| Undecane | 3.39 | 1139583 | 0 | 100.0 |
| Dodecane | 4.16 | 17065669 | 1858091 | 89.1 |
| Dodecene isomer | 4.39 | 9997068 | 770380 | 92.3 |
| Dodecene isomer | 4.45 | 5165264 | 370370 | 92.8 |
| Dodecene isomer | 4.49 | 1864387 | 224856 | 87.9 |
| Dodecene isomer | 4.60 | 6606623 | 518956 | 92.1 |
| Dodecene isomer | 4.69 | 4871544 | 384054 | 92.1 |
| Tridecane | 4.89 | 434688 | 91475 | 79.0 |
| Tetradecane | 5.58 | 6864662 | 841425 | 87.7 |
| Tetradecene isomer | 5.78 | 1799963 | 134020 | 92.6 |
| Tetradecene isomer | 5.84 | 580558 | 50299 | 91.3 |
| Tetradecene isomer | 5.88 | 235342 | 34614 | 85.3 |
| Tetradecene isomer | 5.97 | 729601 | 44650 | 93.9 |
| Tetradecene isomer | 6.06 | 559398 | 209913 | 62.5 |
| Pentadecane | 6.23 | 151876 | 28738 | 81.1 |
| Methyl 4,6-decadienyl ether | 6.61 | 2127943 | 169814 | 92.0 |
| Hexadecane | 6.84 | 1055440 | 307915 | 70.8 |
| 1-Chlorododecane | 7.31 | 932377 | 120438 | 87.1 |
| Alkyl Benzene | 7.72 | 646264 | 42187 | 93.5 |
| Alkyl Benzene | 7.79 | 732825 | 62895 | 91.4 |
| Alkyl Benzene | 7.95 | 825458 | 70947 | 91.4 |
| Alkyl Benzene | 8.22 | 158968 | 19055 | 88.0 |
| Alkyl Benzene | 8.28 | 857712 | 82212 | 90.4 |
| Alkyl Benzene | 8.34 | 313335 | 14071 | 95.5 |
| Alkyl Benzene | 9.35 | 120877 | 0 | 100.0 |
| Dodecanol | 8.87 | 20170340 | 8855647 | 56.1 |
| Tetradecanol | 9.85 | 5956311 | 2885441 | 51.6 |
| Hexadecanol | 10.77 | 515519 | 352413 | 31.6 |
| | | | Average % Reduction | 84.3 |

Example V

Dentifrice Compositions

Dentifrice compositions according to the present invention are shown below as Examples Va-Vi in Table 8. These compositions contain surfactants resulting from the process set forth herein in Examples I-IV. Such compositions have improved taste versus compositions containing the untreated commercially available water-soluble surfactants.

TABLE 8

Dentifrice Examples

| Ingredient | Va | Vb | Vc | Vd | Ve | Vf | Vg | Vh | Vi |
|---|---|---|---|---|---|---|---|---|---|
| Carbomer 956 | 0.2 | | | 0.3 | 0.2 | 0.2 | 0.2 | 0.2 | 0.2 |
| CMC | | 0.75 | 0.2 | | | 1.0 | 1.0 | 1.0 | 1.0 |
| Color Solution (1%) | 0.05 | 0.05 | 0.50 | 0.75 | 0.18 | 0.02 | 0.25 | 0.05 | 0.05 |
| Wintergreen Spice Flavor | | | | | 0.15 | | | | |
| Fruit Mint Flavor | | 0.55 | | | | | | | |
| Mint Flavor | 0.59 | | 0.45 | | 0.42 | 1.0 | 1.2 | 1.0 | 1.0 |
| Cinnamon Flavor | | | | 0.5 | | | | | |
| WS-23 | | | 0.02 | 0.05 | 0.02 | | | | |
| WS-3 | | | 0.02 | 0.05 | 0.02 | | | | |
| MGA | | | | 0.2 | | | | | |
| Menthol | 0.52 | 0.55 | 0.56 | 0.15 | 0.58 | | | | |
| G-180 | 0.01 | 0.03 | 0.015 | 0.004 | 0.01 | 0.01 | 0.03 | 0.008 | 0.02 |
| Potassium Sorbate | | | | | | 0.004 | 0.008 | 0.004 | 0.004 |
| Poloxamer 407 | | | 1.0 | | 0.2 | 0.2 | 0.2 | 0.2 | 0.2 |
| Polyethylene Glycol 300 | 3.0 | 3.0 | | 3.00 | | | | | |
| Polyethylene Glycol 600 | | | 2.3 | | | | | | |
| Propylene Glycol | | | 10.0 | | | | | | |
| Sweetener | 0.46 | 0.5 | 0.45 | 0.4 | 0.58 | 0.4 | 0.4 | 0.4 | 0.4 |
| Silica Abrasive | 22.0 | 31.0 | 20.0 | 21.0 | 17.0 | 15.0 | 15.0 | 15.0 | 15.0 |
| Sodium Benzoate | | | | | | 0.004 | 0.004 | 0.004 | 0.004 |
| Silica Thickening | | | 2.0 | | | 7.0 | 7.0 | 7.0 | 7.0 |
| Sodium Bicarbonate | | 1.50 | 9.0 | | | | | | |
| Sodium Carbonate | | 0.50 | | | | | | | |
| NaOH 50% Soln | | | 1.74 | 2.20 | | 2.0 | 2.0 | 2.0 | 2.0 |
| Na Lauryl Sulfate according to Example IV | 4.0 | 5.0 | 3.0 | 4.0 | 4.0 | | | 3.0 | 2.0 |
| Sodium Fluoride | | | | | | 0.243 | 0.243 | 0.243 | |
| Sodium MFP | 0.76 | 0.76 | 0.76 | 0.76 | 0.76 | | | | 0.76 |
| Glycerin USP 99.7% | 9.0 | 11.9 | 33.0 | 9.0 | | | | | |
| Sorbitol Soln USP | 24.3 | 24.5 | 4.0 | 44.7 | 56.9 | 43.0 | 43.0 | 40.0 | 38.0 |
| Tetra Na Pyrophosphate, Anhydrous | 2.05 | 5.045 | 3.85 | | 3.85 | | | | |
| Tetra Potassium Pyrophosphate (60% Soln) | 6.38 | | | | | | | | |
| Na Acid Pyrophosphate | 2.1 | | | 4.0 | 1.0 | 4.3 | 4.5 | 4.5 | 2.0 |
| Mono Alkyl Phosphate according to Example I | | | | | | 3.5 | 6.7 | 3.5 | 3.5 |
| Cocamidopropyl Betaine (30% soln) according to Example II | | | | | | 3.5 | | | |
| Titanium Dioxide | 0.5 | | 1.0 | | 0.25 | 0.3 | 0.3 | 0.2 | 0.2 |
| TiO$_2$/Carnauba Wax Prills | | 0.6 | | 0.3 | | | | | |
| Xanthan Gum | 0.6 | | 0.4 | 0.45 | 0.7 | 0.3 | 0.3 | 0.3 | 0.3 |
| Water | QS | QS | QS | QS | QS | QS | QS | QS | QS |

Example VI

Improved Ethoxylated Mono Alkyl Phosphate Surfactant

Undesirable non-polar materials were extracted from ethoxylated mono alkyl phosphate (supplied by Rhodia) utilizing a high pressure carbon dioxide to separate the non-polar materials from the ethoxylated mono alkyl phosphate. First, 45 ml of the surfactant was placed into a 100 cc processing bag. The bag was then engulfed by an additional 100 cc sample processing bag filled with 6 mm glass beads. The bags filled with the surfactant and glass beads were placed into a 100 cc sample processing vessel (200 C/10 kspi operation) of the SFE unit. The settings used were: 80° C. for the oven assembly and restrictor valve assembly. The tank pressure with CO2 was brought to 750 psi and equilibrated for 10-15 minutes. Then the pressure was set to 3500 psi and allowed to soak for 10 minutes. After 10 minutes, the static/dynamic valve was opened and CO2 flow was maintained at a steady rate of 10 mL/min for 10 min Alternating static soaking and dynamic flow steps were completed 10 times at the same pressure and temperature conditions.

The extracted materials were then analyzed and the treated ethoxylated mono alkyl phosphate surfactant was evaluated for taste and odor after the extraction and shown to be very mild, especially when compared with the starting material. The undesirable materials identified as removed from the commercially supplied material are set forth in Table 9, below.

TABLE 9 ethoxylated mono alkyl phosphate - Pre and Post CO2 Extraction

| # | Sample Description | CO2 Extraction Conditions | Concentration of undesirable materials (ppm, µg/g) | | |
|---|---|---|---|---|---|
| | | | Dodecanal | Dodecanol | Dodecyl Acetate |
| VIa | DERMALCARE MAP L213/S | Untreated | 94.3 | 6534.0 | 62.0 |
| VIb | DERMALCARE MAP L213/S | Post-Extraction 3500 Psi/80° C. | 75.6 | 5256.8 | 47.6 |

Sample VIa shows the untreated surfactant had 94.3 ppm Dodecanal, 6534 ppm dodecanol, and 62 ppm dodecyl acetate. After treating the surfactant in a batch CO2 process as described, the treated MAP sample VIb contained a reduced dodecanal of 75.6 ppm, a reduced dodecanol of 5256.8 ppm, and a reduced dodecyl acetate of 47.6 ppm.

Example VII

Improved Amine Oxide Surfactant

Undesirable non-polar materials were extracted from N,N-Dimethyldodecylamine N-oxide (amine oxide) surfactant (~30% aqueous solution), supplied by Sigma-Aldrich Corporation (St. Louis, Mo., USA), using the process steps shown in Example I, substituting the amine oxide for the MAP L213/S. Additionally, a different rotary evaporator (model EL131 supplied by BUCHI Labortechnik AG in Flawil, Switzerland) was used for removing residual EtOAc. During rotovap, a vacuum was also applied via rough pump (General Electric model SKC36PN435GX, Fort Wayne, Ind., USA), which was controlled by manual adjustment of a clamp added to a teed in segment of hose between the pump inlet and rotovap. Vacuum was increased to the point where surfactant began gentle bubbling. By applying vacuum, the rate of residual EtOAc removal was significantly increased. The pre- and post-extraction amine oxide materials were then analyzed by immersion SPME GC-MS (Agilent model 7890 GC & model 5975 Mass Spectrometric Detector, Agilent Technologies, Wilmington, Del., USA), and the treated amine oxide surfactant was evaluated for taste and odor after the extraction and shown to be very mild, especially when compared with the starting material. GC-MS analyses for this example were performed at a later time with newer equipment and the resulting retention times are slightly longer than for other examples. The undesirable materials removed from the commercially supplied material are set forth in Table 10, below.

TABLE 10

Results for Amine Oxide LLE treatment with EtOAc

| Undesirable Material | Retention Time (Min) | Control (Pre-extract) Peak Area | Post Extract Peak Area | Area Reduction (%) |
|---|---|---|---|---|
| Decane | 3.45 | 729450 | 0 | 100.0 |
| N,N-Dimethylhydroxylamine | 4.198 | 5799292 | 0 | 100.0 |
| Undecane | 4.326 | 1.58E+08 | 0 | 100.0 |
| Undecene Isomer | 4.613 | 2433592 | 0 | 100.0 |
| Undecene Isomer | 4.663 | 514924 | 0 | 100.0 |
| Undecene Isomer | 4.696 | 4576558 | 0 | 100.0 |
| Undecene Isomer | 4.731 | 3314628 | 0 | 100.0 |
| Undecene Isomer | 4.873 | 13478025 | 0 | 100.0 |
| Undecene Isomer | 4.981 | 7185801 | 0 | 100.0 |
| Dodecane | 5.262 | 97542837 | 275259 | 99.7 |
| Dodecene Isomer | 5.517 | 1722855 | 0 | 100.0 |
| Dodecene Isomer | 5.564 | 256787 | 0 | 100.0 |
| Dodecene Isomer | 5.594 | 1970807 | 0 | 100.0 |
| Dodecene Isomer | 5.637 | 1.34E+08 | 20278565 | 84.9 |
| Dodecene Isomer | 5.686 | 1713571 | 0 | 100.0 |
| Dodecene Isomer | 5.749 | 5157893 | 0 | 100.0 |
| Dodecene Isomer | 5.847 | 2337409 | 0 | 100.0 |
| Tridecane | 6.079 | 60387770 | 0 | 100.0 |
| Substituted Tetrahydrofuran | 6.211 | 741293 | 0 | 100.0 |
| Tridecene Isomer | 6.304 | 934388 | 0 | 100.0 |
| Tridecene Isomer | 6.373 | 2370074 | 0 | 100.0 |
| Tridecene Isomer | 6.411 | 1509006 | 0 | 100.0 |
| Tridecene Isomer | 6.514 | 5357518 | 0 | 100.0 |
| Tridecene Isomer | 6.61 | 2493787 | 0 | 100.0 |
| Tetradecane | 6.808 | 88989028 | 0 | 100.0 |
| Tetradecene Isomer | 7.013 | 648872 | 0 | 100.0 |
| Tetradecene Isomer | 7.075 | 793547 | 0 | 100.0 |
| Tetradecene Isomer | 7.119 | 51889810 | 6298997 | 87.9 |
| Methyl Tetradecane Isomer | 7.184 | 1406294 | 0 | 100.0 |
| Tetradecene Isomer | 7.209 | 1387502 | 0 | 100.0 |
| Tetradecene Isomer | 7.301 | 1082259 | 0 | 100.0 |
| Pentadecane | 7.469 | 10662978 | 0 | 100.0 |
| Unknown | 7.683 | 3450057 | 0 | 100.0 |
| Methyl 4,6-decadienyl ether | 7.863 | 19513653 | 0 | 100.0 |
| Hexadecane | 8.094 | 34907941 | 0 | 100.0 |
| Undecanone Isomer | 8.166 | 258835 | 0 | 100.0 |
| N,N-Dimethyl-1-Dodecanamine | 8.304 | 76976187 | 228611 | 99.7 |
| Undecanol | 8.381 | 5483997 | 0 | 100.0 |
| Dimethyl Undecanone | 8.421 | 1533470 | 0 | 100.0 |
| Dodecanone Isomer | 8.582 | 394239 | 0 | 100.0 |
| Heptadecane | 8.681 | 4445134 | 0 | 100.0 |
| Dodecanone Isomer | 8.783 | 537729 | 0 | 100.0 |
| Dodecanal | 8.824 | 16858547 | 3586725 | 78.7 |
| Substituted Tetrahydrofuran | 8.956 | 4420861 | 0 | 100.0 |
| Methyl 6,8-dodecadienyl ether | 9.056 | 13713367 | 0 | 100.0 |
| Octadecane | 9.238 | 23859062 | 0 | 100.0 |
| Dodecanoic acid, methyl ester | 9.303 | 6560940 | 0 | 100.0 |
| N,N-Dimethyl-1-Tetradecanamine | 9.358 | 26094804 | 3499984 | 86.6 |
| Tetradecanone Isomer | 9.737 | 1458218 | 0 | 100.0 |
| Nonadecane | 9.768 | 1489949 | 0 | 100.0 |
| Unknown Amide | 9.864 | 255865 | 0 | 100.0 |
| Tetradecanone Isomer | 9.923 | 589980 | 0 | 100.0 |
| Unknown Amide | 10.048 | 341466 | 0 | 100.0 |
| Dodecanol | 10.137 | 40526459 | 856635 | 97.9 |
| Pentadecanone Isomer | 10.273 | 4602974 | 0 | 100.0 |
| Methyl tetradecanoate | 10.374 | 1435045 | 0 | 100.0 |
| Pentadecanone Isomer | 10.451 | 1668318 | 0 | 100.0 |
| Tetradecanol | 11.128 | 9874928 | 0 | 100.0 |
| N,N-Dimethyldodecanamide | 12.113 | 44118371 | 65123 | 99.9 |
| p-Dicyclohexylbenzene | 12.445 | 2523931 | 0 | 100.0 |
| N,N-Dimethyltetradecanamide | 13.048 | 14118245 | 679312 | 95.2 |
| Dodecanoic acid ester | 14.154 | 24988729 | 0 | 100.0 |
| Dodecanoic acid ester | 15.662 | 2168393 | 0 | 100.0 |
| | | | Avg % Reduction = | 98.9 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 g" is intended to mean "about 20 g." All percentages, ratios and proportions herein are on a weight basis unless otherwise indicated. Except as otherwise noted, all amounts including quantities, percentages, portions, and proportions, are not intended to indicate significant digits.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Except as otherwise noted, the articles "a", "an", and "the" mean "one or more".

As used herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for improving the taste of water-soluble surfactants using liquid-liquid solvent extraction, said process comprising the steps of:
   a) providing a water-soluble surfactant composition wherein said water-soluble surfactant composition comprises a water-soluble surfactant and one or more undesirable non-polar materials;
   b) contacting said water-soluble surfactant composition with an extraction solvent and water to form an extraction mixture comprising an aqueous phase and a solvent phase; and
   c) separating the aqueous phase from the solvent phase;
wherein the extraction solvent is selected from solvents having individual Hansen solubility parameters of a dispersion force component ($\delta_D$) ranging from about 13 to about 19 $(MPa)^{0.5}$, a polar component ($\delta_P$) ranging from 0 to about 9 $(MPa)^{0.5}$ and a hydrogen bonding component ($\delta_H$) ranging from 0 to about 11 $(MPa)^{0.5}$.

2. A process according to claim 1 wherein the water-soluble surfactant is at least about 20% soluble in water.

3. A process according to claim 1 wherein the water-soluble surfactant is selected from anionic surfactants, zwitterionic surfactants, amphoteric surfactants, and mixtures thereof and is at least about 30% soluble in water.

4. A process according to claim 1 wherein the water-soluble surfactant is selected from alkyl phosphate surfactants, alkyl phosphate ethoxylated surfactants, lauryl sulfate surfactants, betaine surfactants, betaine ethoxylated surfactants, amine oxide surfactants, and mixtures thereof.

5. A process according to claim 1, wherein the surfactant is selected from cocoamidopropyl betaines, alkyl ethoxylated phosphates, mono alkyl phosphates, and mixtures thereof.

6. A process according to claim 1 wherein the extraction solvent has individual Hansen solubility parameters of a dispersion force component ($\delta_D$) ranging from about 15 to about 17 $(MPa)^{0.5}$, a polar component ($\delta_P$) ranging from about 2 to about 9 $(MPa)^{0.5}$ and a hydrogen bonding component ($\delta_H$) ranging from about 2 to about 11 $(MPa)^{0.5}$.

7. A process according to claim 1 wherein the extraction solvent is selected from ethyl acetate, water-saturated ethyl acetate, ethyl propionate, ethyl butyrate, ethyl pentanoate, ethyl caproate, ethyl caprylate, ethyl pelargonate, methyl acetate, methyl propionate, methyl butyrate, short chain esters, supercritical carbon dioxide, and mixtures thereof.

8. A process according to claim 7 wherein the extraction solvent is selected from food grade ethyl esters.

9. A process according to claim 5, wherein the extraction solvent is ethyl acetate.

10. A process according to claim 1 wherein the extraction mixture comprises from about 10% to about 90%, by weight of the mixture, of water; from about 5% to about 60%, by weight of the mixture, of water-soluble surfactant; less than 5%, by weight of the mixture, of undesirable non-polar impurities; and from about 10% to about 90%, by weight of the mixture, of solvent.

11. A process according to claim 10, wherein the ratio of extraction solvent to water-soluble surfactant in the extraction mixture is from about 1:10 to about 10:1.

12. A process according to claim 1 wherein the step of separating the aqueous phase from the solvent phase further comprises centrifuging the extraction mixture.

13. A process according to claim 1 wherein the process further comprises mixing the extraction mixture for a period of from about 10 seconds to about one minute with vigorous mixing and at ambient temperature before allowing the mixture to settle into two phases and separating the aqueous phase from the solvent phase.

14. A process according to claim 1 wherein the process further comprises the step of heating a solid impure surfactant material to its melting point before the step of contacting with an extraction solvent and water.

15. A process according to claim 1 wherein the process further comprises the step of removing any residual solvent from the aqueous phase wherein the step of removing any residual solvent from the aqueous phase includes the use of an industrial method selected from vacuum stripping (with or without heat), fractional distillation, wiped-film evaporator, carbon filtration, and combinations thereof.

16. A process according to claim 1 wherein the extraction mixture further comprises a phase separation enhancer selected from salt, pH modifiers, and mixtures thereof.

17. A process for improving the taste of water-soluble surfactants using liquid-liquid solvent extraction, said process comprising the steps of:

a) providing a water-soluble surfactant composition comprising a surfactant selected from alkyl phosphate surfactants, alkyl phosphate ethoxylated surfactants, and mixtures thereof and one or more undesirable non-polar materials;
b) contacting said water-soluble surfactant composition with ethyl acetate and water to form an extraction mixture comprising an aqueous phase and a solvent phase; and
c) separating the aqueous phase from the solvent phase.

18. A process for improving the taste of water-soluble surfactants using liquid-liquid solvent extraction, said process comprising the steps of:
a) providing a water-soluble surfactant composition wherein said water-soluble surfactant composition comprises a water-soluble surfactant and one or more undesirable non-polar materials;
b) contacting said water-soluble surfactant composition with an extraction solvent and water to form an extraction mixture comprising an aqueous phase and a solvent phase; and
c) separating the aqueous phase from the solvent phase;
wherein the extraction solvent is selected from ethyl acetate, water-saturated ethyl acetate, ethyl propionate, ethyl butyrate, ethyl pentanoate, ethyl caproate, ethyl caprylate, ethyl pelargonate, methyl acetate, methyl propionate, methyl butyrate, short chain esters, supercritical carbon dioxide, and mixtures thereof.

19. A process according to claim 18 wherein the extraction solvent is selected from food grade ethyl esters.

20. A process according to claim 19, wherein the extraction solvent is ethyl acetate.

21. A process for improving the taste of water-soluble surfactants using liquid-liquid solvent extraction, said process comprising the steps of:
a) providing a water-soluble surfactant composition wherein said water-soluble surfactant composition comprises a surfactant selected from alkyl phosphate surfactants, alkyl phosphate ethoxylated surfactants, and mixtures thereof and one or more undesirable non-polar materials;
b) contacting said water-soluble surfactant composition with an extraction solvent and water to form an extraction mixture comprising an aqueous phase and a solvent phase; and
c) separating the aqueous phase from the solvent phase;
wherein the extraction solvent is selected from ethyl acetate, water-saturated ethyl acetate, ethyl propionate, ethyl butyrate, ethyl pentanoate, ethyl caproate, ethyl caprylate, ethyl pelargonate, methyl acetate, methyl propionate, methyl butyrate, short chain esters, supercritical carbon dioxide, and mixtures thereof.

22. A process according to claim 5 wherein the water-soluble surfactant is an alkyl ethoxylated phosphate surfactant.

* * * * *